US007425457B2

(12) United States Patent
Tokutake et al.

(10) Patent No.: US 7,425,457 B2
(45) Date of Patent: Sep. 16, 2008

(54) METHOD AND APPARATUS FOR IRRADIATING SIMULATED SOLAR RADIATION

(75) Inventors: Nobuo Tokutake, Nara (JP); Akio Hasebe, Nara (JP)

(73) Assignee: Canon Kabushiki Kaisha, Tokyo (JP)

( * ) Notice: Subject to any disclaimer, the term of this patent is extended or adjusted under 35 U.S.C. 154(b) by 1152 days.

(21) Appl. No.: 10/792,715

(22) Filed: Mar. 5, 2004

(65) Prior Publication Data

US 2004/0174691 A1 Sep. 9, 2004

(30) Foreign Application Priority Data

Mar. 7, 2003 (JP) ............................ 2003-061614

(51) Int. Cl.
*H01L 21/66* (2006.01)
*G01R 31/26* (2006.01)
*A61N 5/06* (2006.01)

(52) U.S. Cl. ....................... 438/17; 324/765; 250/494.1

(58) Field of Classification Search .................. 438/14, 438/17; 324/765; 250/494.1
See application file for complete search history.

(56) References Cited

U.S. PATENT DOCUMENTS

| | | | | |
|---|---|---|---|---|
| 3,555,351 | A | 1/1971 | Sherwin | 315/154 |
| 4,417,182 | A | 11/1983 | Weber | 315/210 |
| 4,641,227 | A | 2/1987 | Kusuhara | 362/231 |
| 5,740,314 | A * | 4/1998 | Grimm | 392/420 |
| 5,924,784 | A | 7/1999 | Chliwnyj et al. | 362/234 |
| 5,942,048 | A | 8/1999 | Fujisaki et al. | 136/256 |
| 6,051,778 | A | 4/2000 | Ichinose et al. | 136/256 |
| 6,154,034 | A | 11/2000 | Lovelady et al. | 324/501 |
| 6,169,414 | B1 | 1/2001 | Yoshino et al. | 324/767 |
| 6,548,819 | B1 * | 4/2003 | Lovelady | 250/495.1 |
| 7,071,476 | B2 * | 7/2006 | Rothweiler et al. | 250/492.2 |
| 2004/0020529 | A1 | 2/2004 | Schutt et al. | 136/245 |

FOREIGN PATENT DOCUMENTS

| | | |
|---|---|---|
| EP | 1 139 016 | 10/2001 |
| JP | 61-269801 | 11/1986 |
| JP | 11-26785 | 1/1999 |
| JP | 11-214165 | 6/1999 |
| WO | WO 02/03053 | 1/2002 |
| WO | 100 51 357 | 4/2002 |

* cited by examiner

*Primary Examiner*—Scott B. Geyer
*Assistant Examiner*—Seahvosh J Nikmanesh
(74) *Attorney, Agent, or Firm*—Fitzpatrick, Cella, Harper & Scinto

(57) ABSTRACT

In a method of irradiating an object with simulated solar radiation using a plurality of light sources, the object is irradiated with simulated solar radiation resulting from superimposed light rays from a plurality of light sources including light sources having different times at which light emission output reaches a peak.

38 Claims, 13 Drawing Sheets

METHOD AND APPARATUS FOR IRRADIATING SIMULATED SOLAR RADIATION

BACKGROUND OF THE INVENTION

1. Field of the Invention

The present invention relates to a method and apparatus for irradiating an object with temporally stable light, and more particularly, to a method and apparatus for irradiating simulated solar radiation, which needs to be irradiated in large light quantity and over a large area, in temporally stable light quantity and spectrum. The present invention also relates to a method and apparatus for irradiating a semiconductor device which is an object temporally responding relatively quickly to a temporal variation in light quantity over a sensitive wavelength range with temporally stable light.

2. Related Background Art

As a method for irradiating a semiconductor device with simulated solar radiation, Japanese Patent Application Laid-Open No. S61-269801 discloses a method of lighting and irradiation using a xenon lamp as a light source, using an expensive air mass filter for adjusting a spectral distribution and using an expensive stabilized DC power supply as a power supply source. Though this method is costly, it can secure temporal stability of light quantity relatively easily and is appropriate for a case where an object to be irradiated is small and the total price falls within an allowable range. However, the price of this method increases at an accelerating pace as the required irradiation area grows. This is because attempting to irradiate the entire surface of an object with substantially uniform light in response to an increase of the area of the object requires increases in size of components such as the air mass filter and other optical systems, which increases the degree of difficulty of manufacturing in an accelerating pace and further requires an increase in the capacity of the expensive stabilized DC power supply for the lamp, which is costly from the very beginning.

As one of methods for realizing a large area, Japanese Patent Application Laid-Open No. H11-26785 discloses a method for lighting a lamp using pulses. This method is effective in terms of reducing the capacity of a power supply for the lamp. However, the necessity for large size components such as an air mass filter and other optical systems remains the same and this method is still costly. Moreover, while this method takes into account the temporal stability of light quantity during a pulse lighting-up time, it ignores the temporal stability of continuous light quantity including a non-lighting-up time.

SUMMARY OF THE INVENTION

As described above, according to the conventional technologies, when an attempt is made to irradiate an object with temporally stable light, the price of the apparatus increases as the light quantity and the area increase or such temporal stability must be unavoidably ignored, all of which make the method difficult to realize in practice.

It is an object of the present invention to provide a method and apparatus for irradiating an object with temporally stable light at low cost and using actually feasible means. More specifically, it is an object of the present invention to provide a method and apparatus for irradiating simulated solar radiation, which needs to be irradiated in large light quantity and over a large area, with temporally stable light quantity and spectrum. It is another object of the present invention to provide a method and apparatus for irradiating a semiconductor device which is an object responding relatively quickly to a temporal variation in light quantities over a sensitive wavelength range, with temporally stable light.

In order to attain the above-described objects, a method and apparatus for irradiating light according to the present invention is characterized by irradiating an object with simulated solar radiation resulting from superimposed light rays from a plurality of light sources including light sources having different times at which light emission output reaches a peak.

Furthermore, a light irradiation apparatus used for a characteristic test of a semiconductor device of the present invention is characterized in that an object is irradiated with light resulting from superimposed light rays from a plurality of light sources including light sources having different times at which light emission output reaches a peak.

Furthermore, a method of testing characteristics of a semiconductor device with a light irradiating step of the present invention is characterized by including a step of irradiating a semiconductor device with light resulting from superimposed light rays from a plurality of light sources including light sources having different times at which light emission output reaches a peak.

The light sources having different times at which light emission output reaches a peak are preferably light sources having a plurality of light-emitting seeds with different time constants.

The light sources having different times at which light emission output reaches a peak are preferably discharge lamps and more preferably mercury lamps or metal halide lamps.

The output waveforms of the light sources having different times at which light emission output reaches a peak are preferably substantially similar or substantially periodic.

The energy supply sources of the light sources having different times at which light emission output reaches a peak are preferably single-phase AC, two-phase AC or three-phase AC.

The phase difference of light emission output peaks of the light sources having different times at which light emission output reaches a peak is preferably an integer multiple of 1/n of 180 degrees, where n is the number of light sources or the number of light source groups having different times at which light emission output reaches a peak.

The arrangement of the light sources having different times at which light emission output reaches a peak preferably includes an arrangement of m-gon, where m is an integer multiple of n and n is the number of light sources or the number of light source groups having different times at which light emission output reaches a peak. A linear arrangement is also preferable.

The arrangement of the light sources having different times at which light emission output reaches a peak is preferably set in such a way that when the number of light sources or the number of light source groups having different times at which light emission output reaches a peak is 2, the ratio of a sum total of irradiation light quantities of light sources or light source groups having different times at which one light emission output reaches a peak to a sum total of irradiation light quantities of light sources or light source groups having different times at which other light emission outputs reach a peak is 0.82 to 1.22 as a standard for an object to be irradiated.

Furthermore, the arrangement of the light sources having different times at which light emission output reaches a peak is preferably set in such a way that when the number of light sources or the number of light source groups having different times at which light emission output reaches a peak is 3, the ratio of a sum total of irradiation light quantities of light sources or light source groups having different times at which one light emission output reaches a peak to a sum total of irradiation light quantities of light sources or light source groups having different times at which other light emission outputs reach a peak is 1:0.75 to 1.33 as a standard for an object to be irradiated.

DESCRIPTION OF THE PREFERRED EMBODIMENTS

Figure 1:
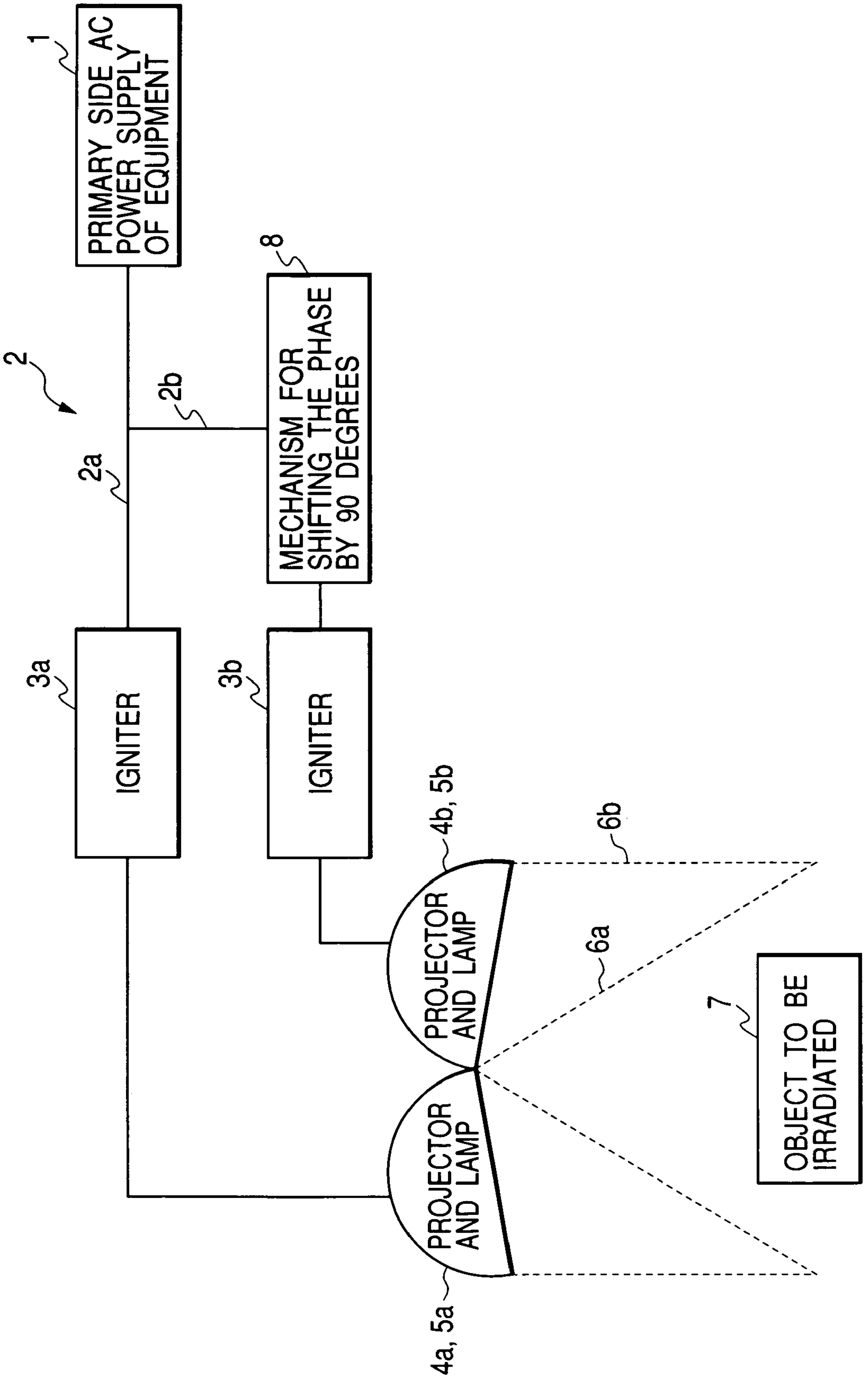
FIG. 1 is a schematic view of a method and apparatus for irradiating light according to first embodiment of the present invention.

Preferred embodiments of the present invention will be explained below, but the present invention is not limited to these embodiments.

<Optical System>

With regard to a light source, on the premise that a plurality of light sources are used, it is possible to select various types of light sources in consideration of the light quantity required, irradiation area required and spectral distribution required, etc. According to the present invention, it is possible to use a light source which, when lit with an AC through an igniter, has excellent temporal responsivity to a power supply variation with its light emission output sensitively varying in a cycle double the AC frequency because it is lit with an AC. For example, it is also possible to use a discharge lamp like a mercury lamp which can easily obtain large light quantity. Furthermore, it is also preferable to use a metal halide lamp, etc., which can easily obtain large light quantity and for which a spectral distribution is also currently being improved. Furthermore, according to the present invention, a light source having a plurality of light-emitting seeds with different time constants such as a metal halide lamp can secure necessary temporal stability in a spectral distribution, and is therefore a preferable light source. Here, a “time constant of a light-emitting seed” in this Specification means a time required to attenuate from peak intensity to a value of certain percentage (e.g., 1/e of peak intensity).

It is possible to use various optical parts such as condenser, reflector, integrator, collimator lens, spectral correction filter, diffusing filter, light-shielding plate as required for the optical system. Furthermore, it is also preferable to use an optical unit such as a projector whose upsizing is relatively easy to incorporate the above-described plurality of light sources in one unit.

<Energy Supply System>

Various types of energy can be used for the energy supply system. For a stable power supply, it is preferable to supply power supplied from a power company as a primary side AC power supply of the equipment. Furthermore, it is also preferable to supply power through a power generator using various types of fuel such as petroleum and gas because a two-phase AC can be easily supplied in this way. Moreover, DC power can also be supplied from a battery, etc.

Using an AC power supply such as single-phase AC, two-phase AC, three-phase AC to supply energy is preferable because it is possible to supply substantially similar, substantially periodic energy in this way. It is also preferable to provide a mechanism which temporally shifts light emission output peaks of a light source at some part of an energy supply route as required. Two-phase AC and three-phase AC are preferable because they have components with different phases from the beginning.

Furthermore, it is also possible to supply energy in a pulsated form by temporarily storing charge in a capacitor.

<Light Emission Output>

Various light emission outputs can be obtained by combining various types of light source, optical system and energy supply system. Then, it is possible to irradiate an object with temporally stable light by superimposing light rays from light sources having different times at which light emission output reaches a peak. As light emission output to be focused, it is possible to set light quantity in an entire wavelength range, light quantity for each predetermined wavelength range defined by a standard, etc., light quantity in a wavelength range having sensitivity to an object to be irradiated, etc., depending on the purpose of use of this method and apparatus for irradiating light as appropriate.

Output waveforms of light sources having different times at which light emission output reaches a peak are preferably substantially similar when consideration is given to ease of control. It is also preferably substantially periodic. Such waveforms are preferable because they can be obtained easily by selecting, for example, AC power as the energy supply system and combining light sources whose light emission output is also sensitively variable in a cycle double an AC frequency because they are lit with an AC as the light sources.

Various levels of the temporal stability of light quantity irradiated with light resulting from superimposed light rays from light sources having different times at which light emission output reaches a peak are selected according to the purpose of use. For example, with regard to a solar simulator (simulated solar radiation irradiation apparatus for a photovoltaic device) used for testing a photovoltaic device, IEC60904-9 describes the required performance of spectral coincidence to be satisfied in the area used of the surface to be irradiated, in-plane variation of irradiance and temporal stability. With regard to the temporal stability, class A is within ±2%, class B is within ±5% and class C is within ±10%. To be qualified as having passed a test verifying the required performance in compliance with IEC60904-9, it is necessary to use a light irradiation apparatus that satisfies the performance also in the aspect of temporal stability of light quantity.

Thus, the temporal stability of light quantity irradiated to an object is preferably within ±10%.

At this time, in order to irradiate the object to be irradiated with light in temporally stable light quantity, it is possible to set an arrangement of a plurality of light sources by trial and error, but it is preferable that an appropriate arrangement standard be made settable because this can reduce the total adjustment load drastically. A variation of light emission output can be divided into a ground light emission component as a minimum value of light emission output and a variable component added thereto. As opposed to a case of responding to a variation of energy with which the light emission output whose ground light emission component is substantially 0 is supplied more sensitively, the ratio of the variation width of light emission output to average light emission output is improved by the effect of the ground light emission component and decreases as the ground light emission component increases. In other words, when attention is focused on the ground light emission component, it is possible to set a more appropriate standard by estimating the light emission output whose ground light emission component is substantially 0 as a basis.

Furthermore, various levels of temporal stability of a spectral distribution irradiated with light resulting from superimposed light rays from light sources having different times at which light emission output reaches a peak can also be selected depending on the purpose of use thereof. With regard to spectral coincidence set for each predetermined wavelength range in aforementioned IEC60904-9, class A is within a range of 0.75 to 1.25, class B is within a range of 0.6 to 1.4 and class C is within a range of 0.4 to 2.0. To be qualified as having passed a test verifying the required performance in compliance with IEC60904-9, it is necessary to use a light irradiation apparatus that satisfies the performance also in the aspect of temporal stability in spectral coincidence.

Thus, the temporal stability of spectral coincidence irradiated to an object is preferably within a range of 0.4 to 2.0.

At this time, when attention is focused on a spectral distribution, a light source having a plurality of light-emitting seeds with different time constants, in response to a variation of energy with which the light emission output of a light-emitting seed whose time constant is substantially 0 is supplied more sensitively, the variation width of the light emission output is improved by the temporal averaging effect by the time constant and decreases as the time constant of the light-emitting seed increases. In other words, when attention is focused on a difference in the time constant, it is possible to set a more appropriate standard by estimating the light emission output whose time constant is substantially 0 as a basis.

When energy which is the square of a sine wave is supplied from an energy supply system and light emission output is obtained according to the energy, that is, when the ground light emission component and time constant are regarded as substantially 0, a case where light rays from two light sources having different times at which light emission output reaches a peak is as shown in the following example.

TABLE 1

| | | | | | |
|---|---|---|---|---|---|
| 0 degree (reference) | 1.00 | 1.00 | 1.00 | 1.00 | 1.00 |
| Amplitude ratio of 90 degrees | 1.00 | 0.95 | 0.90 | 0.85 | 0.82 |
| Temporal stability of irradiation light quantity of superimposed light (±%) | 0 | 3 | 5 | 8 | 10 |

The phase of a quasi-sine wave of one light source was set to 0 degree as a reference and the phase of a quasi-sine wave of the other light source was set to 90 degrees. In Table 1, the temporal stability of irradiation light quantity of superimpose light was checked by changing the amplitude ratio of the light source with the phase of the quasi-sine wave set to 90 degrees to the light source with the phase of the quasi-sine wave set to 0 degree. That is, the light source with the phase of the quasi-sine wave set to 0 degree and light source with the phase of the quasi-sine wave set to 90 degrees only differ in the amplitude and are substantially similar. To satisfy a range of within ±10%, an amplitude ratio up to 0.82 is acceptable. If a reverse reference is adopted, an amplitude ratio up to 1.22 is acceptable.

When energy corresponding to the square of the sine wave is supplied from an energy supply system and light emission output is obtained according to the energy, that is, when the ground light emission component and time constant can be regarded as substantially 0, a case where light rays from three light sources having different times at which light emission output reaches a peak are superimposed is as shown in the following example.

TABLE 2

| | | | | | | | | | |
|---|---|---|---|---|---|---|---|---|---|
| 0 degree (reference) | 1.00 | 1.00 | 1.00 | 1.00 | 1.00 | 1.00 | 1.00 | 1.00 | 1.00 |
| Amplitude ratio of 120 degrees | 1.00 | 1.00 | 1.00 | 1.00 | 0.90 | 0.90 | 0.90 | 0.85 | 0.75 |
| Amplitude ratio of 240 degrees | 1.00 | 0.90 | 0.80 | 0.73 | 0.90 | 0.80 | 0.71 | 0.71 | 0.75 |
| Temporal stability of irradiation light quantity of superimposed light (±%) | 0 | 3 | 7 | 10 | 4 | 6 | 10 | 10 | 10 |

The phase of a quasi-sine wave of one light source was set to 0 degree as a reference and the phases of quasi-sine waves of the other light sources were set to 120 degrees and 240 degrees. In Table 2, the temporal stability of irradiation light quantity of superimpose light was checked by changing the amplitude ratio of the light source with the phase of the quasi-sine wave set to 120 degrees and 240 degrees to the light source with the phase of the quasi-sine wave set to 0 degree. That is, the light sources with the phase of the quasi-sine wave set to 0 degree, 120 degrees and 240 degrees only differ in the amplitude and are substantially similar. To satisfy a range of within ±10%, an amplitude ratio up to 0.71 to 0.75 is acceptable. If a reverse reference is adopted, an amplitude ratio up to 1.41 to 1.33 is acceptable.

(Arrangement of Optical System)

Various types of arrangement can be adopted for an optical system. In order to superimpose light rays from light sources having different times at which light emission output reaches a peak and obtain desired temporal stability efficiently at an object or a surface to be irradiated, it is preferable to adopt an arrangement which prevents the light sources having different times at which light emission output reaches a peak from blocking each other's irradiation optical path.

The number of light sources can be set as required. It is possible to use one set of light sources having different times at which light emission output reaches a peak or form a plurality of light sources having substantially coinciding times at which light emission output reaches a peak as one group and combine it with a group of light sources having different times at which light emission output reaches a peak or combine it with a still further light source. It is desirable to set an arrangement of each light source in consideration of the light quantity irradiated from each light source to each irradiation point and the balance among light quantities irradiated from the respective light source groups. It is further preferable to set the arrangement based on a desirable numerical value range when superimposing light rays from light sources having different times at which the aforementioned light emission output reaches a peak.

At this time, an arrangement of the light sources having different times at which light emission output reaches a peak based on an m-gon, where m is an integer multiple of n and n is the number of light sources or the number of light source groups having different times at which light emission output reaches a peak is preferable because it is easier to balance light quantities within the area in which the object or surface to be irradiated is used. Furthermore, a linear arrangement is also preferable because it is easier to balance light quantities.

(Object to be Irradiated)

Various objects can be used as objects to be irradiated. For example, in the case of a semiconductor device such as a photovoltaic device, responsivity to irradiation light quantity is important and it is preferable to irradiate temporally stable light according to the purpose thereof.

Furthermore, the present invention is preferable because it can irradiate a large-size semiconductor device including a solar cell, solar cell submodule, solar cell module or photovoltaic array, etc., with temporally stable light. The present invention is preferable because it can also irradiate a semiconductor device such as a stacked solar cell which sensitively responds with a spectral distribution using light rays in a wavelength range which varies from one layer to another with light having a temporally stable spectral distribution.

EMBODIMENTS

With reference now to attached drawings, the present invention will be explained using embodiments described below, but the present invention is not limited to these embodiments.

Embodiment 1

Figure 2:
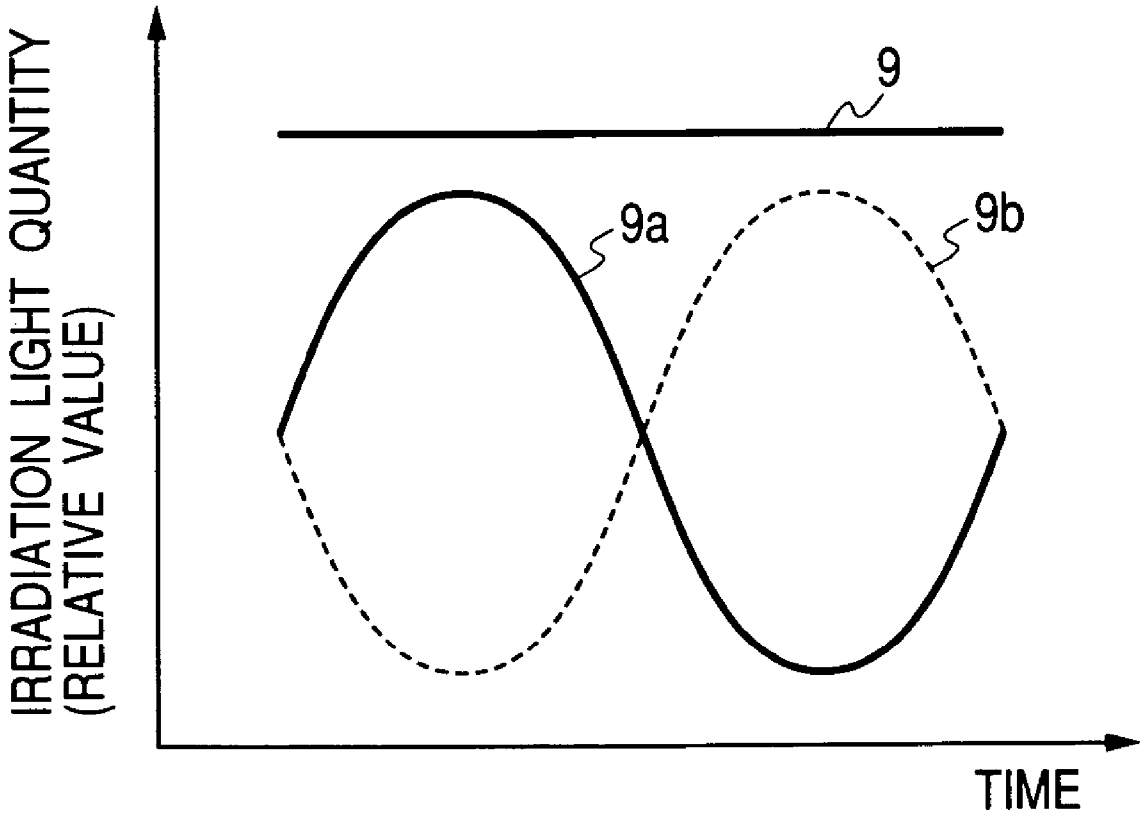
FIG. 2 is a graph showing a relationship between irradiation light quantity acquired at the position of an object to be irradiated according to first and second embodiments of the present invention and time.
Figure 14:
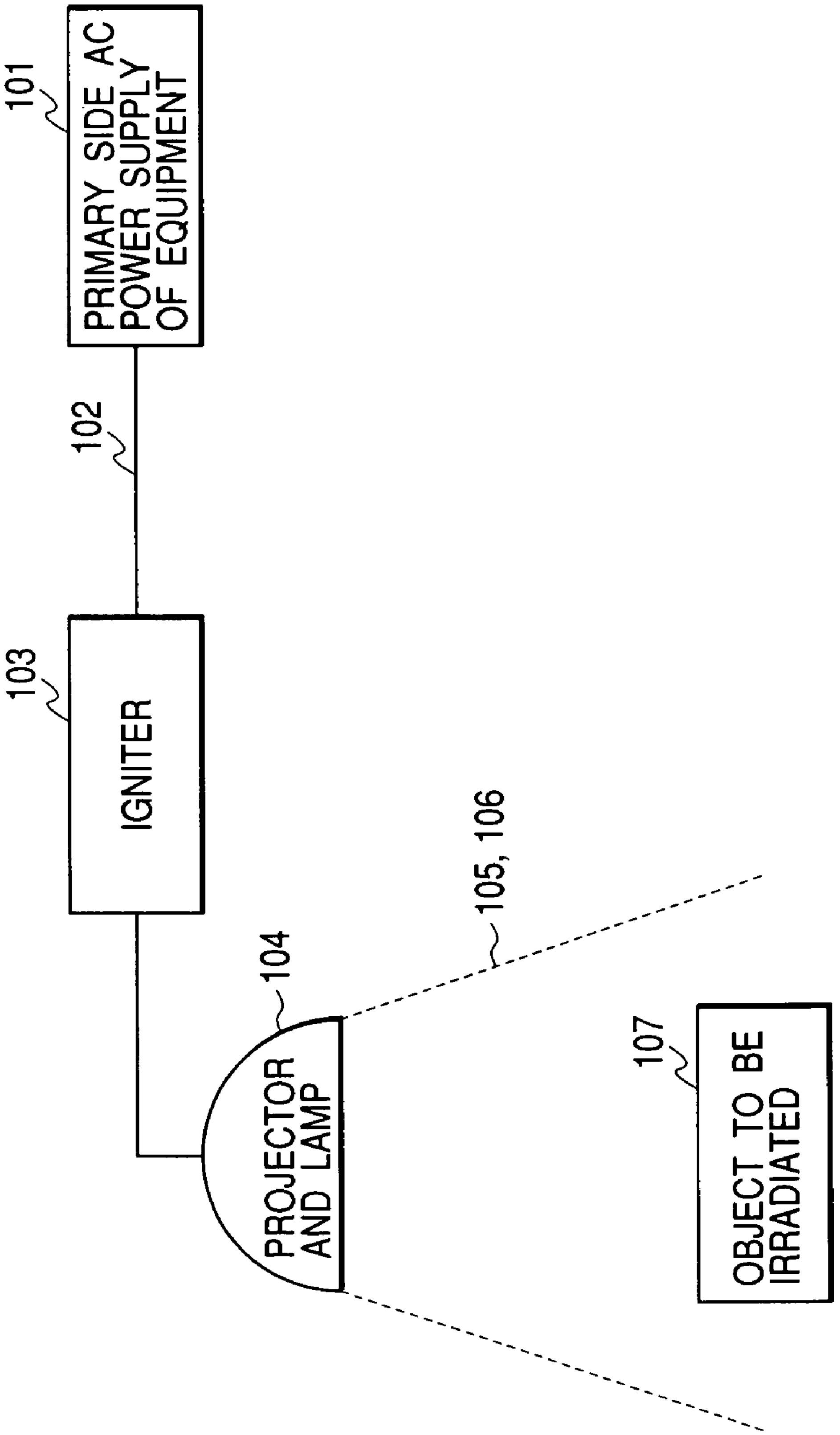
FIG. 14 is a schematic view of a method and apparatus for irradiating light according to comparative example 1.

FIG. 1 is a schematic view of a method and apparatus for irradiating light according to first embodiment of the present invention. FIG. 2 is a graph showing a relationship between irradiation light quantity acquired at the position of the object to be irradiated in FIG. 1 and time. FIG. 14 is a schematic view of a method and apparatus for irradiating light according to comparative example 1 and FIG. 15 is a graph showing a relationship between irradiation light quantity acquired at the position of the object to be irradiated in FIG. 14 and time.

In Embodiment 1 and comparative example 1, a metal halide lamp which is lit with an AC through an igniter was used as a light source. The metal halide lamp can be lit through an inexpensive igniter, it is growing in light quantity and its spectral distribution is being improved, and in this respect the metal halide lamp is a promising simulated solar radiation light source. On the other hand, since it has high temporal responsivity to power supply variations and because it is lit with an AC, its light emission output also varies sensitively in a cycle double the AC frequency and has a plurality of light-emitting seeds with different time constants, thus having the nature that its spectral distribution also varies temporally.

Figure 15:
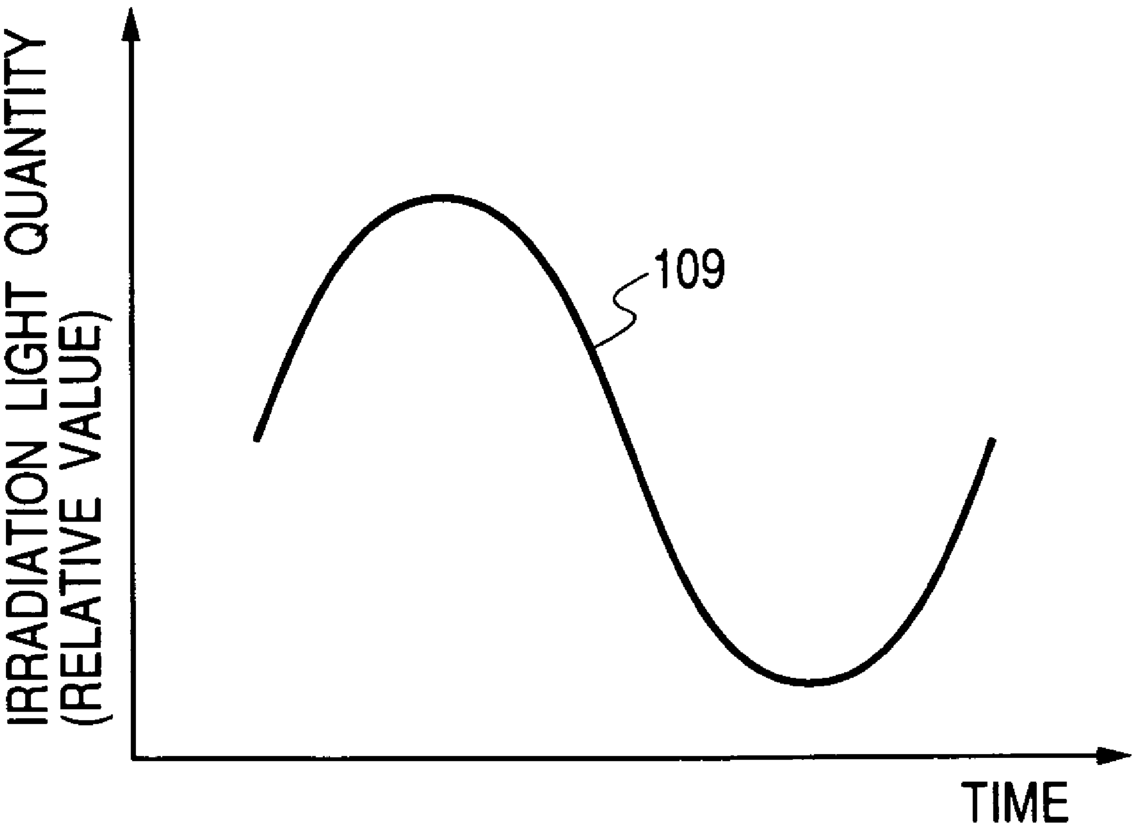
FIG. 15 is a graph showing a relationship between irradiation light quantity acquired at the position of an object to be irradiated according to comparative example 1 and time.

In comparative example 1 shown in FIG. 14 and FIG. 15, power supplied from a primary side AC power supply of equipment 101 is supplied to a lamp 105 in a projector 104 through an electric wiring 102 and an igniter 103. The lamp 105 is lit with an AC and an irradiation light quantity waveform 109 measured at the position of an object to be irradiated 107 also fluctuates in a cycle double the AC frequency.

On the contrary, in Embodiment 1 shown in FIG. 1 and FIG. 2, an AC supplied from a primary side AC power supply of equipment 1 is supplied to lamps 5*a* and 5*b* in two projectors 4*a* and 4*b* through electric wirings 2, 2*a* and 2*b* and igniters 3*a* and 3*b*. However, the phase of the AC supplied to the lamp 5*b* is shifted by 90 degrees by a mechanism 8 for shifting the phase by 90 degrees as some midpoint of the electric wiring 2*b*. The lamps 5*a* and 5*b* are lit with an AC and irradiation light quantity waveforms 9*a* and 9*b* measured at the position of an object to be irradiated 7 obtained when they are lit singly also fluctuate in a cycle double the AC frequency. The irradiation light quantity waveform 9*b* has a different phase, but is a waveform substantially similar to that of the irradiation light quantity waveform 9*a*. If the lamps 5*a* and 5*b* are turned ON simultaneously, since there is a phase difference of 90 degrees of ACs supplied to the two lamps 5*a* and 5*b*, an irradiation light quantity waveform 9 with substantially no temporal variation is obtained. This is the same as the case where attention is focused on the light quantity within a predetermined wavelength range, and as a result, spectral coincidence with substantially no temporal variation is obtained.

In Embodiment 1, the positional relationship between the object to be irradiated 7, two projectors 4*a* and 4*b* and lamps 5*a* and 5*b* are assumed to be an equidistant and symmetric positional relationship. The two projectors 4*a* and 4*b* were tilted toward the object to be irradiated 7. Furthermore, they were arranged so that irradiation light rays from the respective lamps 5*a* and 5*b* and projectors 4*a* and 4*b* to the object to be irradiated 7 were not blocked by the opposite projector or lamp or other objects. This makes the temporally averaged light quantities irradiated from the lamps 5*a* and 5*b* substantially equal over the entire surface of the object to be irradiated 7 and even if the entire surface of the object to be irradiated 7 is divided into smaller areas and measured, it is possible to obtain the irradiation light quantity waveform 9 with substantially no temporal variation.

Furthermore, in order to set the temporal stability of irradiation light quantity of the superimposed light to within ±10%, setting the arrangement of the optical system in such a way that the ratio of the amplitude of the irradiation light quantity waveform 9*a* to the amplitude of the irradiation light quantity waveform 9*b* measured at the position of the object to be irradiated 7 when the lamps are lit singly is set to 1:0.82 to 1.22 as a standard can reduce the total adjustment load drastically and is therefore preferable.

Using the method and apparatus for irradiating light according to Embodiment 1, it is possible to measure, for example, the output of a solar cell module which is a semiconductor device showing quick temporal response to a temporal variation of light quantity. Since irradiation light quantity with substantially no temporal variation is obtained, even a solar cell module which shows quick temporal response produces output with substantially no temporal variation. Therefore, it is possible to measure the output of the solar cell module without-specially performing adjustment of measuring timings and averaging processing of measured values, etc. Furthermore, by changing, for example, the distance between the two lamps 5*a* and 5*b* and the solar cell module or increasing the number of projectors and lamps as required, it is also possible to change the absolute value of irradiation light quantity to the solar cell module or measure the relationship between the output of the solar cell module and irradiation light quantity.

Embodiment 2

Figure 3:
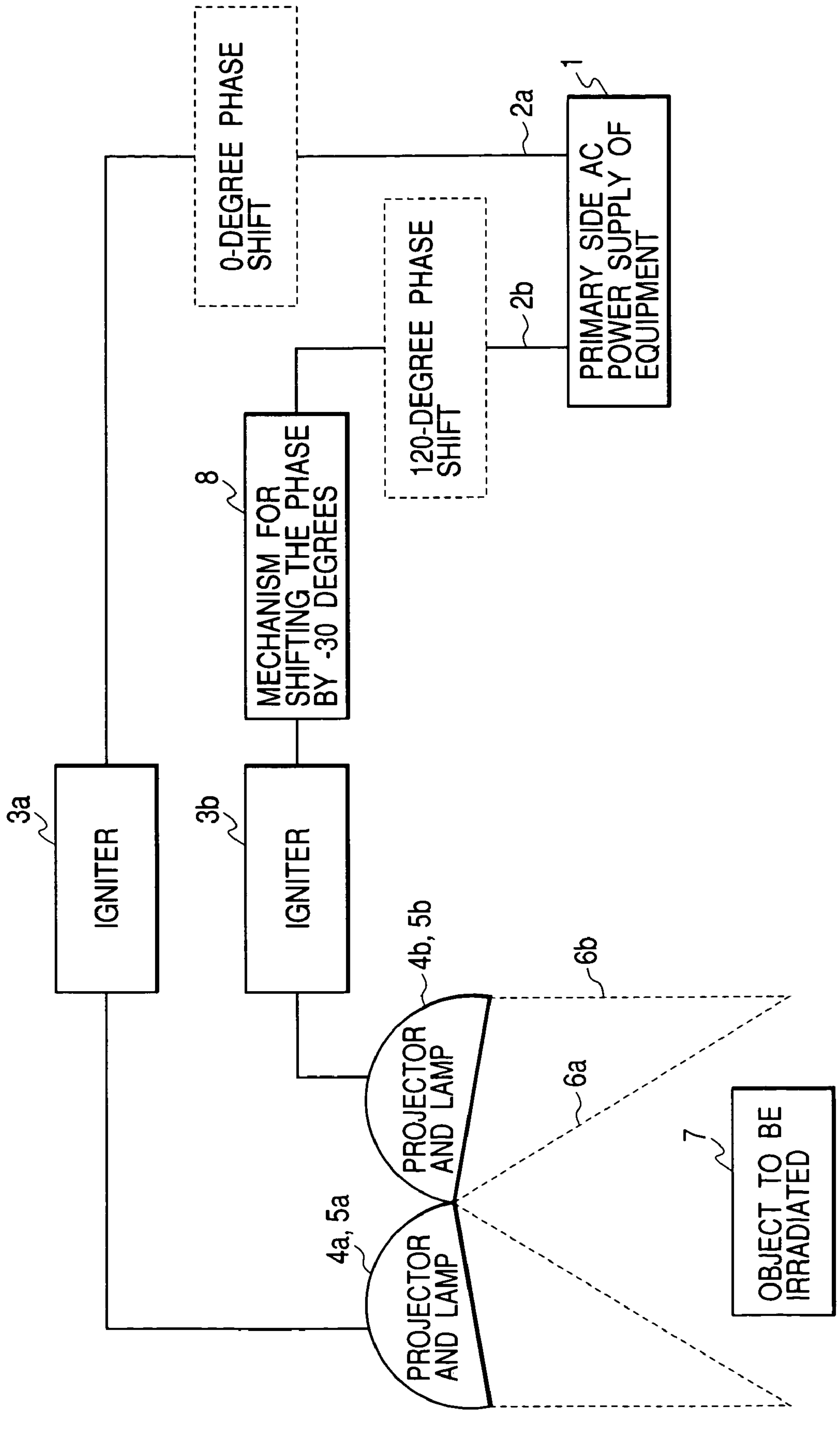
FIG. 3 is a schematic view of a method and apparatus for irradiating light according to second embodiment of the present invention.

FIG. 3 is a schematic view of a method and apparatus for irradiating light according to second embodiment of the present invention. FIG. 2 is a graph showing a relationship between the irradiation light quantity obtained at the position of the object to be irradiated in FIG. 3 and time as in the case of Embodiment 1. This embodiment has a mode of power supply slightly different from that of Embodiment 1 shown in FIG. 1.

In Embodiment 2 shown in FIG. 3, power supplied from a primary side AC power supply of equipment 1 is supplied to lamps 5*a* and 5*b* in two projectors 4*a* and 4*b* through electric wirings 2*a* and 2*b* and igniters 3*a* and 3*b*. As the primary side AC power supply of equipment 1, a three-phase AC is used here. If the phase of the AC supplied to the lamp 5*a* is set as a reference (0 degree), the AC supplied to the lamp 5*b* uses a phase different from the reference phase by 120 degrees and by providing a mechanism 8 for shifting the phase by 30 degrees at some midpoint of the electric wiring 2*b*, the phase is shifted by a total of 90 degrees. The lamps 5*a* and 5*b* are lit with ACs and irradiation light quantity waveforms 9*a* and 9*b* measured at the position of an object to be irradiated 7 obtained when they are lit singly also fluctuate in a cycle double the AC frequency. The irradiation light quantity waveform 9*b* has a different phase, but it is a waveform substantially similar to that of the irradiation light quantity waveform 9*a*. If the lamps 5*a* and 5*b* are turned ON simultaneously, since there is a phase difference of 90 degrees between the ACs supplied to the two lamps 5*a* and 5*b*, an irradiation light quantity waveform 9 with substantially no temporal variation is obtained.

When the method and apparatus for irradiating light according to the present invention is used as actual equipment, it is also possible to adopt the configuration shown in this embodiment for convenience of the primary side AC power supply of the equipment, etc.

Embodiment 3

Figure 4:
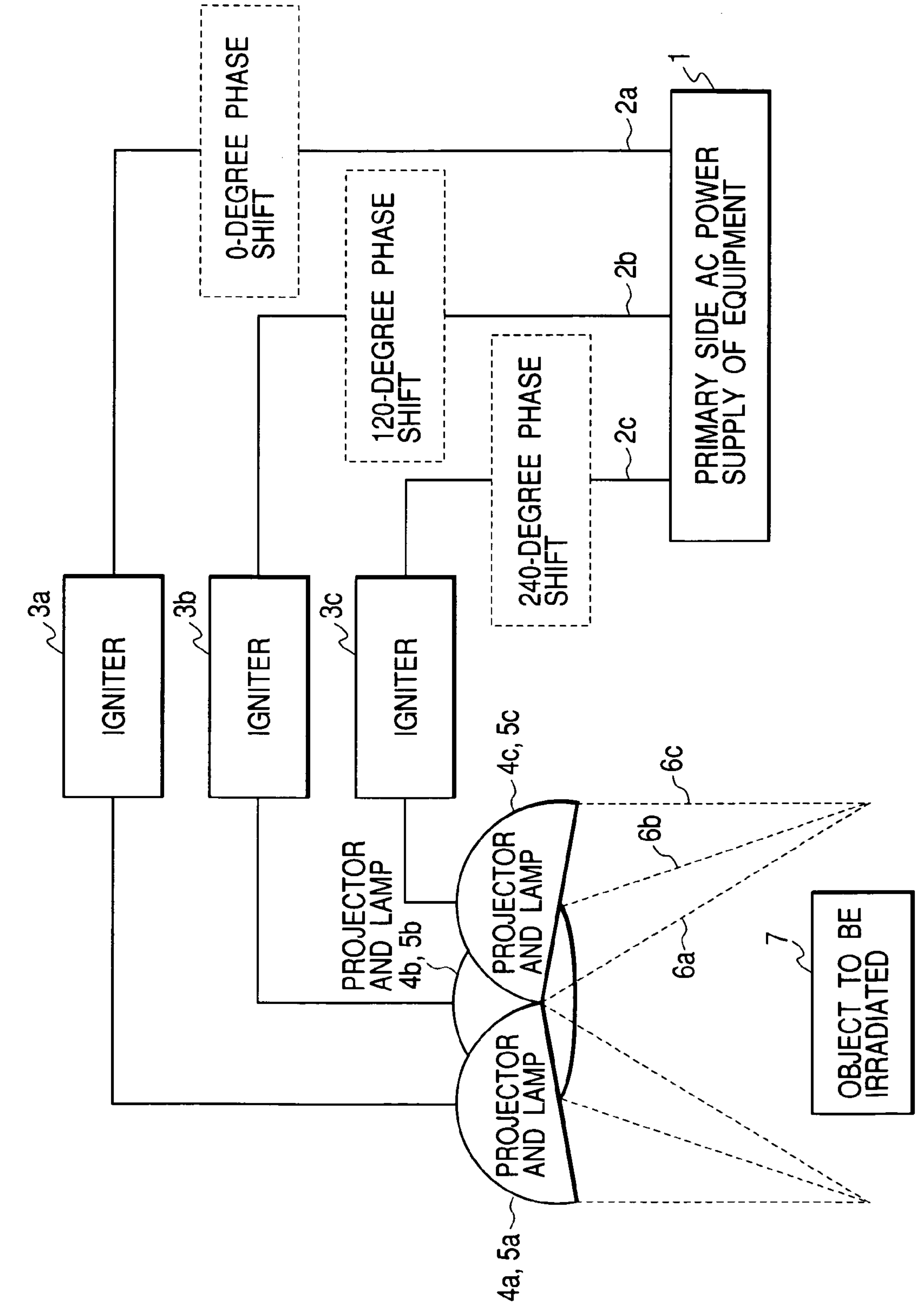
FIG. 4 is a schematic view of a method and apparatus for irradiating light according to third embodiment of the present invention.
Figure 5:
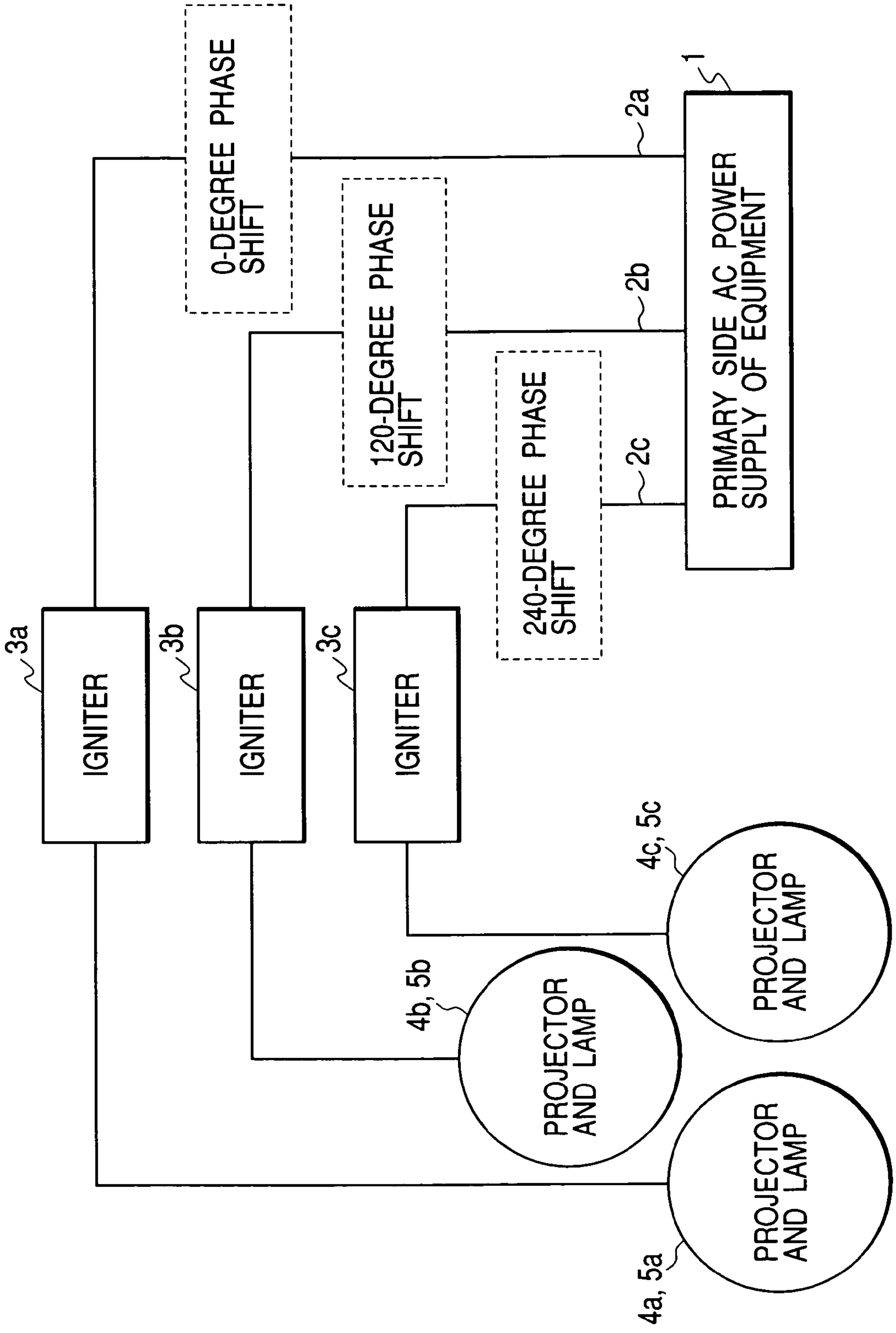
FIG. 5 is a schematic view of the method and apparatus for irradiating light according to third embodiment of the present invention.
Figure 6:
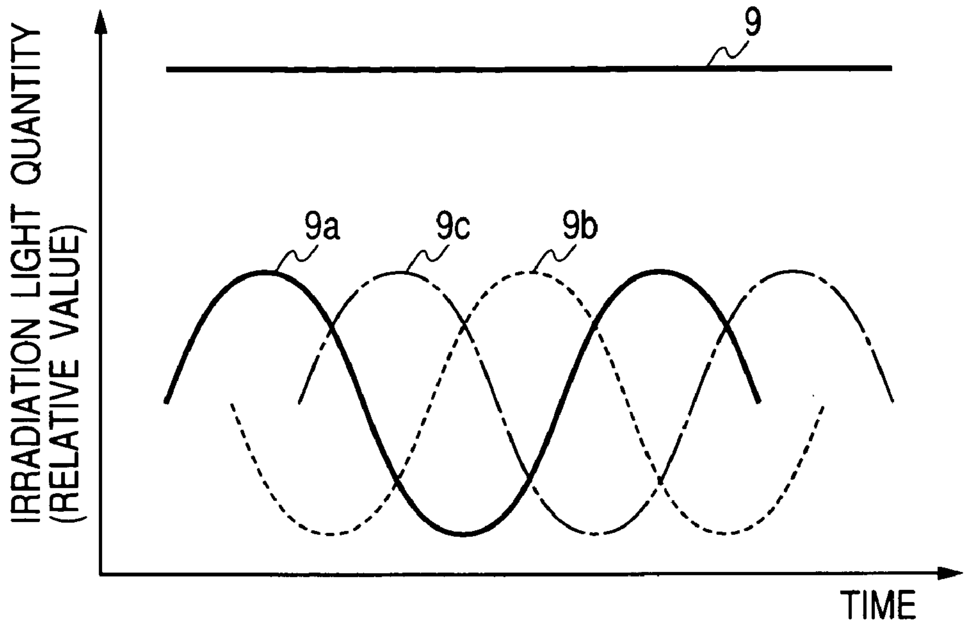
FIG. 6 is a graph showing a relationship between irradiation light quantity acquired at the position of an object to be irradiated according to third embodiment of the present invention and time.

FIG. 4 and FIG. 5 are schematic views of a method and apparatus for irradiating light according to a third embodiment of the present invention. FIG. 6 is a graph showing a relationship between the irradiation light quantity obtained at the position of an object to be irradiated in FIG. 4 and time. As in the case of Embodiment 1, Embodiment 3 also uses a metal halide lamp which is lit with an AC through an igniter as the light source.

In Embodiment 3 shown in FIG. 4, FIG. 5 and FIG. 6, power supplied from a primary side AC power supply of equipment 1 is supplied to lamps 5*a*, 5*b* and 5*c* in three projectors 4*a*, 4*b* and 4*c* through electric wirings 2*a*, 2*b* and 2*c* and igniters 3*a*, 3*b* and 3*c*. As the primary side AC power supply of equipment 1, a three-phase AC is used here. If the phase of the AC supplied to the lamp 5*a* is set as a reference (0 degree), the AC supplied to the lamp 5*b* uses a phase different from the reference phase by 120 degrees and the AC supplied to the lamp 5*c* uses a phase different from the reference phase by 240 degrees. The lamps 5*a*, 5*b* and 5*c* are lit with ACs and irradiation light quantity waveforms 9*a*, 9*b* and 9*c* measured at the position of an object to be irradiated 7 obtained when they are lit singly also fluctuate in a cycle double the AC frequency. The irradiation light quantity waveforms 9*b* and 9*c* have different phases, but are waveforms substantially similar to that of the irradiation light quantity waveform 9*a*. If the lamps 5*a*, 5*b* and 5*c* are turned ON simultaneously, since there are phase differences of 120 degrees and 240 degrees among the ACs supplied to the three lamps 5*a*, 5*b* and 5*c*, an irradiation light quantity waveform 9 with substantially no temporal variation is obtained.

In Embodiment 3, the positional relationship between the object to be irradiated 7 and the three projectors 4*a*, 4*b* and 4*c* and lamps 5*a*, 5*b* and 5*c* is assumed to be an equidistant and symmetric positional relationship. The three projectors 4*a*, 4*b* and 4*c* are tilted toward the object to be irradiated 7. As shown in FIG. 5, the three projectors 4*a*, 4*b* and 4*c* and lamps 5*a*, 5*b* and 5*c* are arranged so as to be located at vertices of a regular triangle. Moreover, the arrangement is made in such a way that the irradiation light rays from the respective lamps 5*a*, 5*b* and 5*c* and projectors 4*a*, 4*b* and 4*c* to the object to be irradiated 7 are not blocked by their opposite projectors and lamps and other object. This makes the temporally averaged light quantities irradiated from the lamps 5*a*, 5*b* and 5*c* substantially equal over the entire surface of the object to be irradiated 7 and even if the entire surface of the object to be irradiated 7 is divided into smaller areas and measured, it is possible to obtain an irradiation light quantity waveform 9 with substantially no temporal variation.

Furthermore, in order to set the temporal stability of irradiation light quantity of the superimposed light to within ±10%, setting the arrangement of the optical system in such a way that the ratio of the amplitude of the irradiation light quantity waveform 9*a* to the amplitudes of the irradiation light quantity waveforms 9*b* and 9*c* measured at the position of the object to be irradiated 7 when the lamps are lit singly is set to 1:0.75 to 1.33 as a standard can reduce the total adjustment load drastically and is therefore preferable.

Embodiment 4

Figure 7:
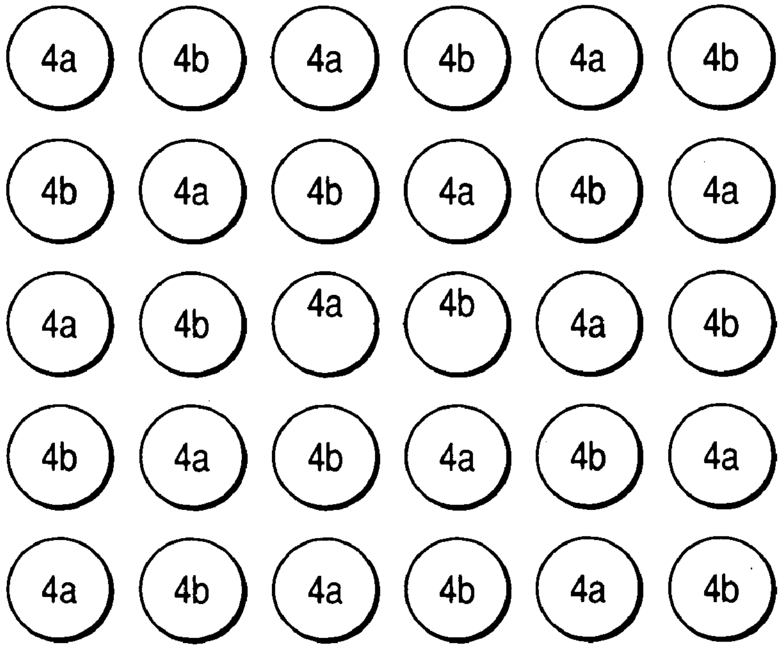
FIG. 7 is a schematic view of a method and apparatus for irradiating light according to fourth embodiment of the present invention.
Figure 8:
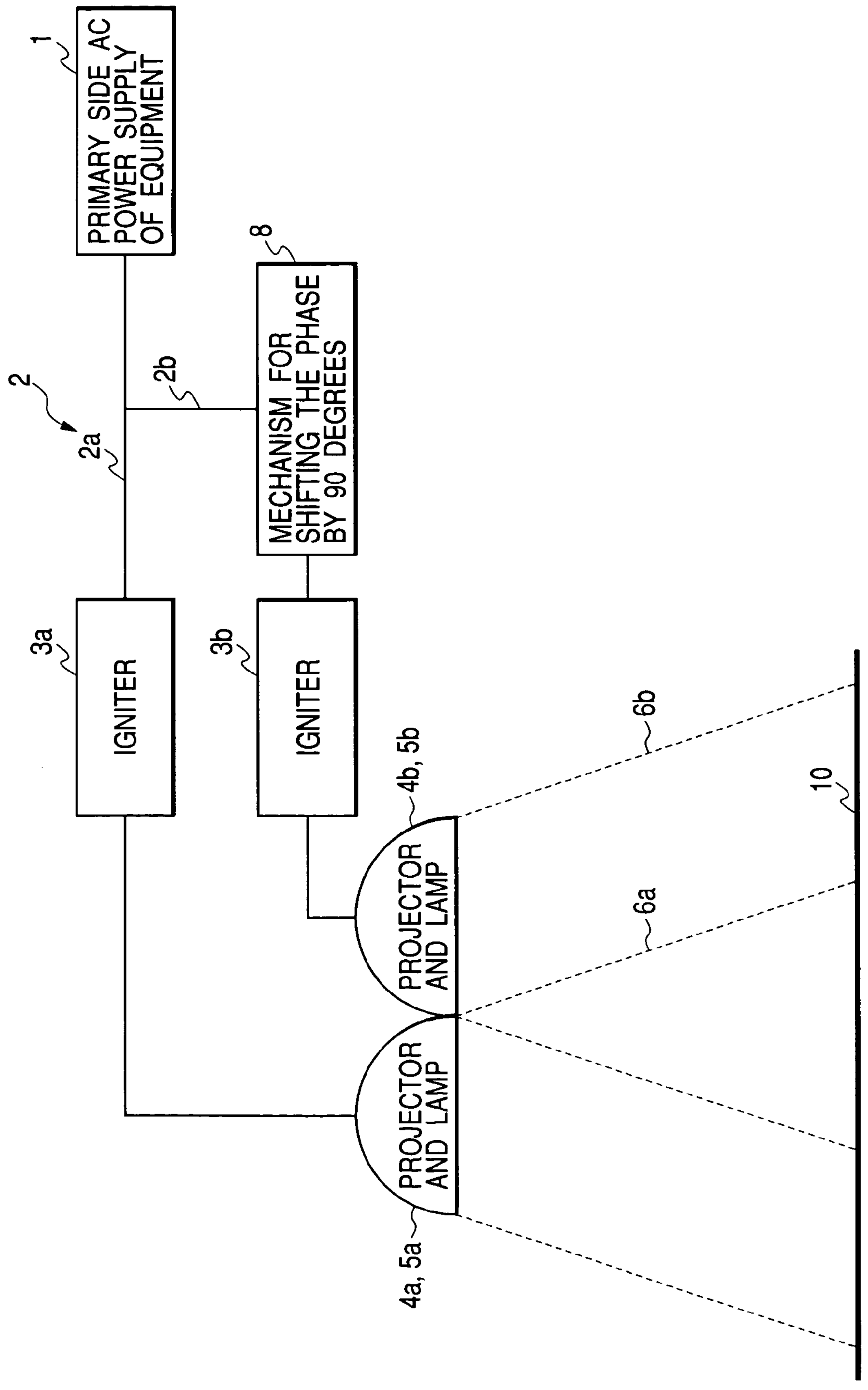
FIG. 8 is a schematic view of the method and apparatus for irradiating light according to fourth embodiment of the present invention.
Figure 9:
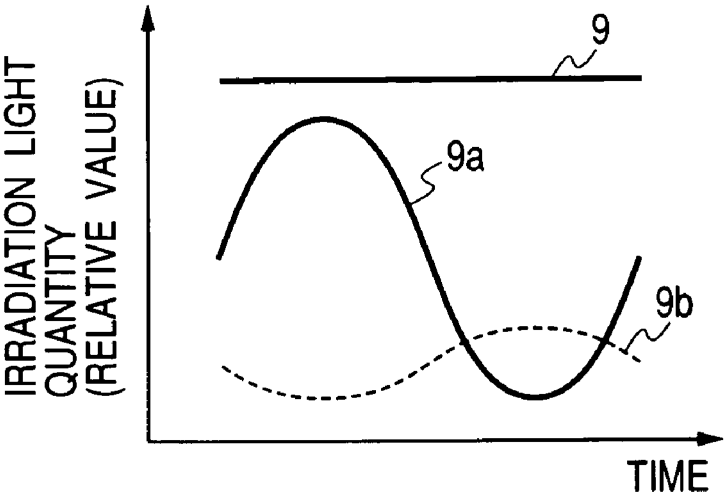
FIG. 9 is a graph showing a relationship between irradiation light quantity acquired at the positions right below a projector 4*a* and a lamp 5*a* according to fourth embodiment of the present invention and time.

FIG. 7 and FIG. 8 are schematic views of a method and apparatus for irradiating light according to fourth embodiment of the present invention. FIG. 7 is a schematic view showing a horizontal arrangement of a plurality of projectors and lamps according to Embodiment 4. FIG. 8 is a schematic view of two sets of projector and lamp, which form a basic unit in FIG. 7. FIG. 9 is a graph showing a relationship between irradiation light quantity obtained right below the projector 4*a* and lamp 5*a* in FIG. 7 and FIG. 8. As in the case of Embodiment 1, Embodiment 4 also uses a metal halide lamp which is lit with an AC through an igniter as the light source.

In Embodiment 4 shown in FIG. 7, FIG. 8 and FIG. 9, power supplied from a primary side AC power supply of equipment 1 is supplied to lamps 5*a* and 5*b* in their respective projectors 4*a* and 4*b* through electric wirings 2*a* and 2*b* and igniters 3*a* and 3*b*. If the phase of the AC supplied to the lamp 5*a* is set as a reference (0 degree), the AC supplied to the lamp 5*b* uses a phase different from the reference phase by 90 degrees. The lamps 5*a* and 5*b* are lit with ACs and irradiation light quantity waveforms 9*a* and 9*b* measured at the positions right below the projector 4*a* and lamp 5*a* obtained when they are lit singly also fluctuate in a cycle double the AC frequency. The irradiation light quantity waveform 9*b* has a different phase and amplitude, but it is substantially similar to that of the irradiation light quantity waveform 9*a*.

In Embodiment 4, the positional relationship between a surface to be irradiated 10 and the two projectors 4*a* and 4*b* and lamps 5*a* and 5*b* is assumed to be an equidistant and symmetric positional relationship. The projectors 4*a* and 4*b* are oriented right below toward the surface to be irradiated 10. As shown in FIG. 7, the two closest basic units; projectors 4*a* and 4*b* and lamps 5*a* and 5*b* are arranged so as to be located at vertices of a square. Furthermore, the arrangement is made so that the irradiation light rays from the respective projectors 4*a* and 4*b* and lamps 5*a* and 5*b* to the surface to be irradiated 10 are not blocked by their nearby projectors and lamps and other objects. This can make the temporally averaged light quantities irradiated from the lamps 5*a* and 5*b* substantially equal right below the projector 4*a* and lamp 5*a* and near an intermediate position right below the projector 4*b* and lamp 5*b*. The light quantity right below one projector and lamp where a light quantity difference is likely to occur in this system is also appropriately adjusted by setting the distance between the projectors 4*a* and 4*b* and between the lamps 5*a* and 5*b*, the distance from the surface to be irradiated 10 in such a way that the ratio of the amplitude of the irradiation light quantity waveform 9*a* to the amplitude of the irradiation light quantity waveform 9*b* measured right below the lamp 5*a* when they are lit singly is substantially set to 1:0.25. If all the lamps 5*a* and 5*b* are lit simultaneously in this condition, the irradiation light quantities from the closest four projectors 4*b* and lamps 5*b* which mainly contribute to the irradiation light quantities surrounding the projector 4*a* and lamp 5*a* are added up even right below the projector 4*a* and lamp 5*a*, and therefore, the amplitude of the irradiation light quantity waveform of the lamp 5*a* is substantially the same as that of a group of the closest lamps 5*b*, that is, the ratio is substantially 1:1, and because the phases of the AC supplied to the lamps 5*a* and 5*b* are different from each other by 90 degrees, an irradiation light quantity waveform 9 with substantially no temporal variation is obtained. This makes the temporally averaged light quantities irradiated from the respective lamps 5*a* and 5*b* substantially equal over the entire area used of the surface to be irradiated 10 and even if the area used of the surface to be irradiated 10 is divided into small areas and measured, it is possible to obtain an irradiation light quantity waveform 9 with substantially no temporal variation.

Furthermore, in order to set the temporal stability of irradiation light quantity of the superimposed light to within +10%, setting the arrangement of the optical system in such a way that the ratio of the amplitude of the irradiation light quantity waveform 9*a* to the amplitude of the irradiation light quantity waveform 9*b* measured at positions right below the projector 4*a* and lamp 5*a* obtained when they are lit singly is set to 1:0.21 (=0.25×0.82) to 0.30 (=0.25×1.22) as a standard can reduce the total adjustment load drastically, which is therefore preferable.

In this embodiment, a total of 15 sets of the projectors 4*a* and 4*b* and lamps 5*a* and 5*b* which are basic units are used, but expanding the same arrangement in FIG. 7 makes it possible to irradiate light of irradiation light quantity with substantially no temporal variation over an arbitrary area. When a large object is irradiated with a large quantity of light, the number of light sources may be increased, but using the present invention makes it possible to irradiate light in irradiation light quantity with substantially no temporal variation at substantially the same cost that would be required when the number of light sources is simply increased. Using the present invention makes it possible to carry out measurements of output of a large solar cell module or a photovoltaic array with a plurality of solar cell modules connected or characteristic tests such as an optical deterioration test.

Embodiment 5

Figure 10:
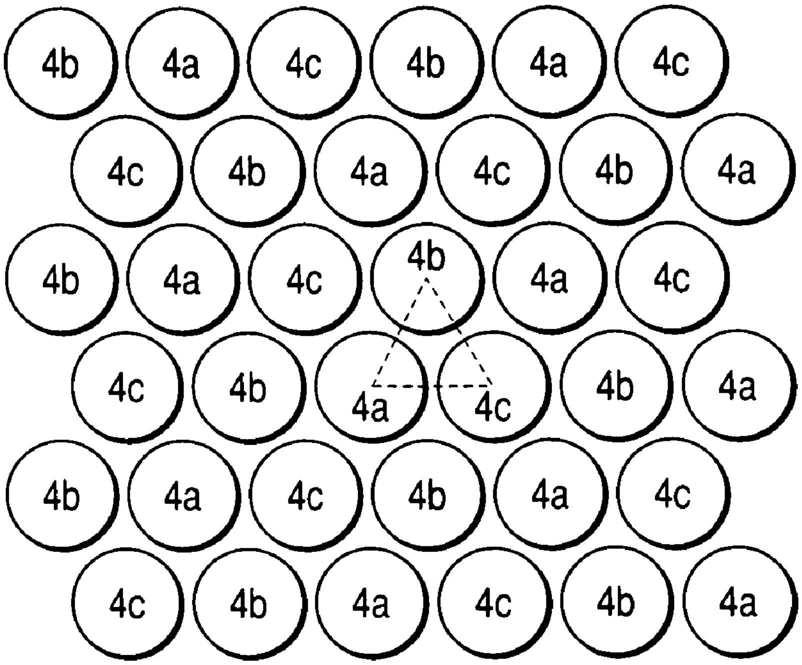
FIG. 10 is a schematic view of a method and apparatus for irradiating light according to fifth embodiment of the present invention.
Figure 11:
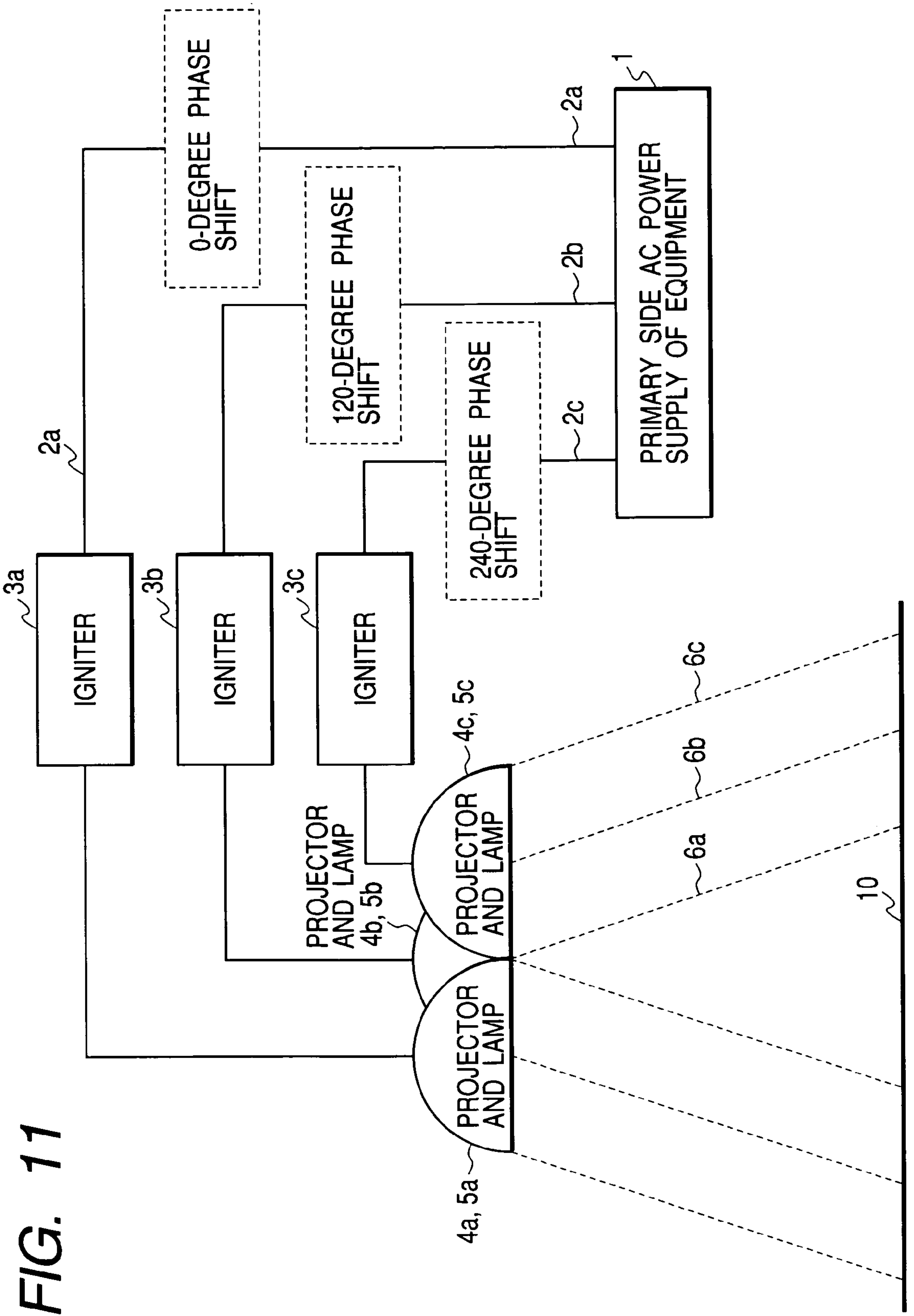
FIG. 11 is a schematic view of the method and apparatus for irradiating light according to fifth embodiment of the present invention.
Figure 12:
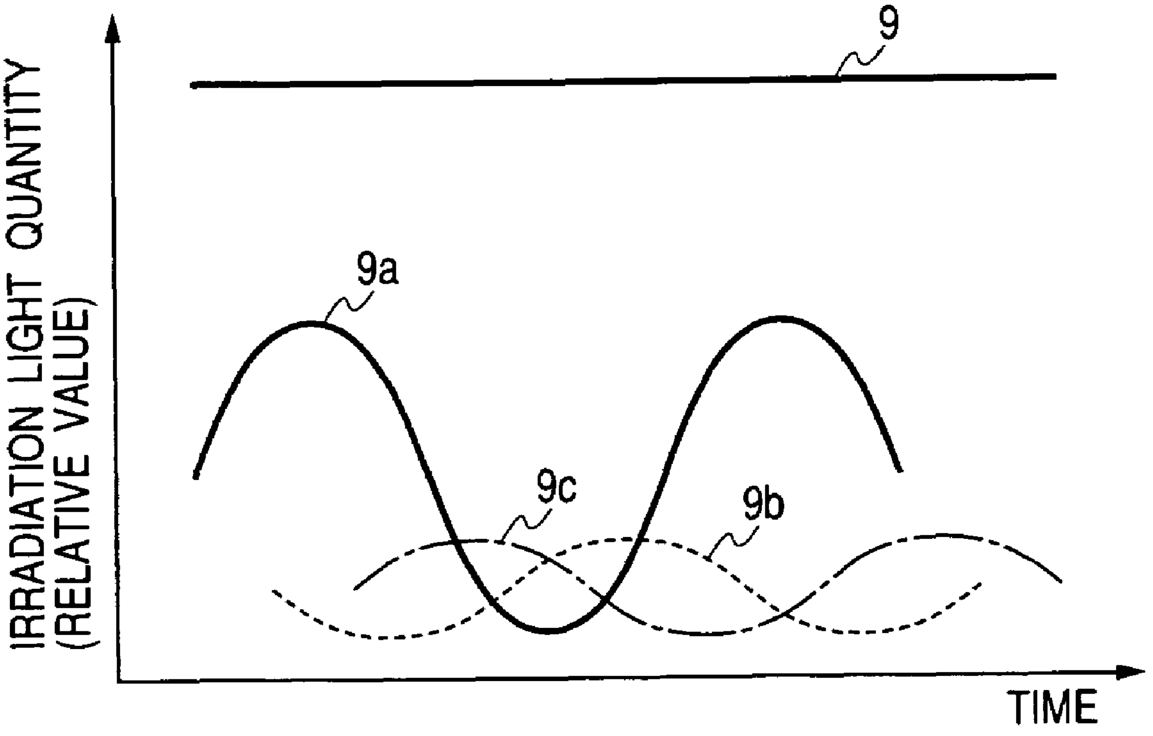
FIG. 12 is a graph showing a relationship between irradiation light quantity acquired at the positions right below a projector 4*a* and a lamp 5*a* according to fifth embodiment of the present invention and time.

FIG. 10 and FIG. 11 are schematic views of a method and apparatus for irradiating light according to fifth embodiment of the present invention. FIG. 10 is a schematic view showing a horizontal arrangement of a plurality of projectors and lamps according to Embodiment 5. FIG. 11 is a schematic view of a set of three projectors and lamps, which form basic units in FIG. 10. FIG. 12 is a graph showing a relationship between irradiation light quantity obtained right below the projector 4*a* and lamp 5*a* in FIG. 10 and FIG. 11 and time. As in the case of Embodiment 1, Embodiment 5 also uses a metal halide lamp which is lit with an AC through an igniter as the light source.

In Embodiment 5 shown in FIG. 10, FIG. 11 and FIG. 12, power supplied from a primary side AC power supply of equipment 1 is supplied to lamps 5*a*, 5*b* and 5*c* in their respective projectors 4*a*, 4*b* and 4*c* through electric wirings 2*a*, 2*b* and 2*c* and igniters 3*a*, 3*b* and 3*c*. Here, a three-phase AC is used as the primary side AC power supply of equipment 1. If the phase of the AC supplied to the lamp 5*a* is set as a reference (0 degree), the AC supplied to the lamp 5*b* uses a phase different from the reference phase by 120 degrees and the AC supplied to the lamp 5*c* uses a phase different from the reference phase by 240 degrees. The lamps 5*a*, 5*b* and 5*c* are lit with ACs and irradiation light quantity waveforms 9*a*, 9*b* and 9*c* measured at positions right below the projector 5*a* and lamp 5*a* obtained when they are lit singly also fluctuate in a cycle double the AC frequency. The irradiation light quantity waveforms 9*b* and 9*c* have different phases and amplitudes, but they are waveforms substantially similar to the irradiation light quantity waveform 9*a*.

In Embodiment 5, the positional relationship between a surface to be irradiated 10 and the three projectors 4*a*, 4*b* and 4*c* and lamps 5*a*, 5*b* and 5*c* is assumed to be an equidistant and symmetric positional relationship. The projectors 4*a*, 4*b* and 4*c* are oriented right below toward the surface to be irradiated 10. As shown in FIG. 10, the three projectors 4*a*, 4*b* and 4*c* are arranged so as to be located at vertices of a regular triangle. Moreover, the arrangement is made in such a way that the irradiation light rays from the respective projectors 4*a*, 4*b* and 4*c* and lamps 5*a*, 5*b* and 5*c* to the surface to be irradiated 10 are not blocked by nearby projectors and lamps and other objects. This makes the temporally averaged light quantities irradiated from the lamps 5*a* and 5*b* substantially equal close to intermediate positions between positions right below the projector 4*a* and lamp 5*a*, right below the projector 4*b* and lamp 5*b* and right below the projector 4*c* and lamp 5*c*. In this system, an appropriate adjustment is made by setting the distances between the projectors 4*a*, 4*b* and 4*c* and lamps 5*a*, 5*b* and 5*c* and the distance from the surface to be irradiated 10 even right below any one projector and lamp, for example, right below the projector 4*a* and lamp 5*a* in such a way that the ratio of the amplitude of the irradiation light quantity waveform 9*a* to the amplitudes of the irradiation light quantity waveforms 9*b* and 9*c* measured at the position right below the projector 4*a* and lamp 5*a* is substantially set to 1:0.33. If all the lamps 5*a*, 5*b* and 5*c* are lit simultaneously in this condition, irradiation light quantities from the three closest projectors 4*a*, 4*b* and 4*c* and lamp 5*a*, 5*b* and 5*c* principally contributing to the irradiation light quantities surrounding the projector 4*a* and lamp 5*a* are added up even right below the projector 4*a* and lamp 5*a*, and therefore, the amplitudes of the irradiation light quantity waveforms from the group of projectors 4*a* and lamps 5*a*, the group of projectors 4*b* and lamps 5*b* and the group of projectors 4*c* and lamps 5*c* are also substantially the same, that is, the ratio is 1:1:1, and because the phases of the ACs supplied to the lamps 5*a*, 5*b* and 5*c* are shifted by 120 degrees and 240 degrees, an irradiation light quantity waveform 9 with substantially no temporal variation is obtained. In this way, the temporally averaged light quantities irradiated from the respective projectors 4*a*, 4*b* and 4*c* and lamps 5*a*, 5*b* and 5*c* are substantially equal over the entire area used of the surface to be irradiated 10, and even if the area used of the surface to be irradiated 10 is divided into small areas and measured, it is possible to obtain the irradiation light quantity waveform 9 with substantially no temporal variation.

Furthermore, in order to set the temporal stability of the irradiation light quantity of the superimposed light to within ±10%, setting the arrangement of the optical system in such a way that the ratio of the amplitude of the irradiation light quantity waveform 9*a* and the amplitudes of the irradiation light quantity waveforms 9*b* and 9*c* measured at positions right below the projector 4*a* and lamp 5*a* obtained when they are lit singly is set to 1:0.25 (=0.33×0.75) to 0.44 (=0.33×1.33) as a standard can reduce the total adjustment load drastically, which is therefore preferable.

This embodiment has used a total of 12 sets of three projectors 4*a*, 4*b* and 4*c* and lamps 5*a*, 5*b* and 5*c* which are basic units, but expanding the same arrangement in FIG. 10 makes it possible to irradiate light in irradiation light quantity with substantially no temporal variation over an arbitrary area. When a large object to be irradiated is irradiated with a large quantity of light, the number of light sources may be increased, but using the present invention makes it possible to irradiate light in irradiation light quantity with substantially no temporal variation at substantially the same cost that would be required when the number of light sources is simply increased. Using the present invention makes it possible to carry out measurements of output of a large solar cell module or a photovoltaic array with a plurality of solar cell modules connected or characteristic tests such as an optical deterioration test.

Embodiment 6

Figure 13:
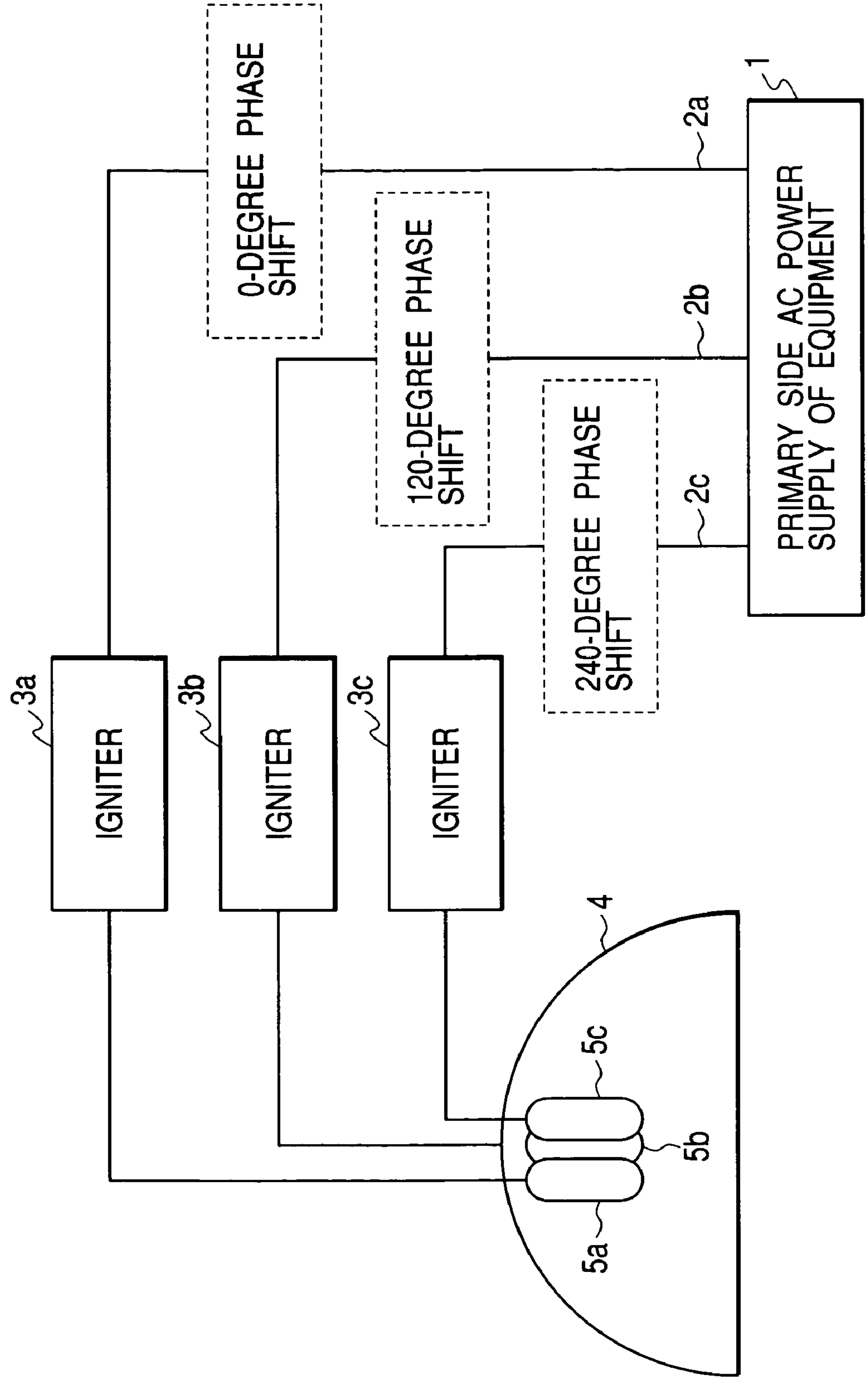
FIG. 13 is a schematic view of a method and apparatus for irradiating light according to sixth embodiment of the present invention.

FIG. 13 is a schematic view of a method and apparatus for irradiating light according to sixth embodiment of the present invention. FIG. 6 is a graph showing a relationship between irradiation light quantity obtained at the position of an object to be irradiated and time. As in the case of Embodiment 1, Embodiment 6 also uses a metal halide lamp which is lit with an AC through an igniter as the light source.

In Embodiment 6 shown in FIG. 13, power supplied from a primary side AC power supply of equipment 1 is supplied to three lamps 5*a*, 5*b* and 5*c* in one large projector 4 through electric wirings 2*a*, 2*b* and 2*c* and igniters 3*a*, 3*b* and 3*c*. Here, a three-phase AC is used as the primary side AC power supply of equipment 1. If the phase of the AC supplied to the lamp 5*a* is set as a reference (0 degree), the AC supplied to the lamp 5*b* uses a phase different from the reference phase by 120 degrees and the AC supplied to the lamp 5*c* uses a phase different from the reference phase by 240 degrees. The lamps 5*a*, 5*b* and 5*c* are lit with ACs and irradiation light quantity waveforms 9*a*, 9*b* and 9*c* measured at the position of the object to be irradiated obtained when they are lit singly also fluctuate in a cycle double the AC frequency. The irradiation light quantity waveforms 9*b* and 9*c* have different phases, but they are waveforms substantially similar to the irradiation light quantity waveform 9*a*. When the lamps 5*a*, 5*b* and 5*c* are lit simultaneously, since the phases of the ACs supplied to the three lamps 5*a*, 5*b* and 5*c* are shifted by 120 degrees and 240 degrees, an irradiation light quantity waveform 9 with substantially no temporal variation is obtained.

In Embodiment 6, the positional relationship between the object to be irradiated and the three lamps 5*a*, 5*b* and 5*c* can be easily set to a positional relationship regarded as an equidistant and symmetric one because the three lamps 5*a*, 5*b* and 5*c* are incorporated in one projector 4. The lamps 5*a*, 5*b* and 5*c* are arranged so as to be located at vertices of a regular triangle in one projector 4. In this way, temporally averaged light quantities irradiated from one projector 4 and lamps 5*a*, 5*b* and 5*c* are substantially equal over the entire surface of the object to be irradiated, and even if the entire surface of the object to be irradiated is divided into small areas and measured, it is possible to obtain an irradiation light quantity waveform 9 with substantially no temporal variation.

As described above, according to the present invention, an object to be irradiated is irradiated with simulated solar radiation resulting from superimposed light rays from a plurality of light sources including light sources having different times at which light emission output reaches a peak. Furthermore, the light irradiation apparatus used for testing characteristics of a semiconductor device is a light irradiation apparatus characterized in that a semiconductor device is irradiated with light resulting from superimposed light rays from a plurality of light sources including light sources having different times at which light emission output reaches a peak. Furthermore, the method of testing characteristics of a semiconductor device including a light irradiating step is a method of testing characteristics of a semiconductor device including a step of irradiating a semiconductor device with light resulting from superimposed light rays from a plurality of light sources including light sources having different times at which light emission output reaches a peak.

As a result, temporally stable light can be irradiated to an object to be irradiated. Especially, simulated solar radiation, which needs to be irradiated in large light quantity and over a large area can be irradiated with light in temporally stable light quantity and spectrum. Furthermore, it is possible to irradiate a semiconductor device which is an object responding relatively quickly to a temporal variation in light quantities over a sensitive wavelength range with temporally stable light.

What is claimed is:

1. A method of irradiating an object with simulated solar radiation resulting from superimposed light rays from a plurality of light sources including light sources having different times at which light emission output reaches a peak.

2. The method of irradiating simulated solar radiation according to claim 1, wherein said light sources having different times at which the light emission output reaches a peak are light sources including a plurality light-emitting seeds with different time constants.

3. The method of irradiating simulated solar radiation according to claim 1, wherein said light sources having different times at which the light emission output reaches a peak are discharge lamps.

4. The method of irradiating simulated solar radiation according to claim 3, wherein said discharge lamps are mercury lamps or metal halide lamps.

5. The method of irradiating simulated solar radiation according to claim 1, wherein the output waveforms of said light sources having different times at which the light emission output reaches a peak are substantially similar.

6. The method of irradiating simulated solar radiation according to claim 1, wherein the output waveforms of said light sources having different times at which the light emission output reaches a peak are substantially periodic.

7. The method of irradiating simulated solar radiation according to claim 1, wherein the energy supply sources of said light sources having different times at which the light emission output reaches a peak are preferably a single-phase AC, two-phase AC or three-phase AC.

8. The method of irradiating simulated solar radiation according to claim 1, wherein the phase difference of light emission output peaks of said light sources having different times at which the light emission output reaches a peak is an integer multiple of 1/n of 180 degrees, where n is the number of light sources or the number of light source groups having different times at which the light emission output reaches a peak.

9. The method of irradiating simulated solar radiation according to claim 1, wherein the arrangement of said light sources having different times at which the light emission output reaches a peak includes an arrangement of m-gon, where m is an integer multiple of n and n is the number of light sources or the number of light source groups having different times at which the light emission output reaches a peak.

10. The method of irradiating simulated solar radiation according to claim 1, wherein the arrangement of said light sources having different times at which the light emission output reaches a peak is linear.

11. The method of irradiating simulated solar radiation according to claim 1, wherein the arrangement of said light sources having different times at which the light emission output reaches a peak is set in such a way that when the number of light sources or the number of light source groups having different times at which the light emission output reaches a peak is 2, the ratio of a sum total of irradiation light quantities of light sources or light source groups having different times at which one light emission output reaches a peak to a sum total of irradiation light quantities of light sources or light source groups having different times at which other light emission outputs reach a peak is 0.82 to 1.22 as a standard for an object to be irradiated.

12. The method of irradiating simulated solar radiation according to claim 1, wherein the arrangement of said light sources having different times at which the light emission output reaches a peak is set in such a way that when the number of light sources or the number of light source groups having different times at which the light emission output reaches a peak is 3, the ratio of a sum total of irradiation light quantities of light sources or light source groups having different times at which one light emission output reaches a peak to a sum total of irradiation light quantities of light sources or light source groups having different times at which other light emission outputs reach a peak is 1:0.75 to 1.33 as a standard for an object to be irradiated.

13. A light irradiation apparatus used for testing characteristics of a semiconductor device, wherein said semiconductor device is irradiated with light resulting from superimposed light rays from a plurality of light sources including light sources having different times at which the light emission output reaches a peak.

14. The light irradiation apparatus according to claim 13, wherein said light sources having different times at which the light emission output reaches a peak are light sources including a plurality light-emitting seeds with different time constants.

15. The light irradiation apparatus according to claim 13, wherein said light sources having different times at which the light emission output reaches a peak are discharge lamps.

16. The light irradiation apparatus according to claim 15, wherein said discharge lamps are mercury lamps or metal halide lamps.

17. The light irradiation apparatus according to claim 13, wherein the output waveforms of said light sources having different times at which the light emission output reaches a peak are substantially similar.

18. The light irradiation apparatus according to claim 13, wherein the output waveforms of said light sources having different times at which the light emission output reaches a peak are substantially periodic.

19. The light irradiation apparatus according to claim 13, wherein energy supply sources of said light sources having different times at which the light emission output reaches a peak are single-phase AC, two-phase AC or three-phase AC.

20. The light irradiation apparatus according to claim 13, wherein the phase difference of light emission output peaks of said light sources having different times at which the light emission output reaches a peak is an integer multiple of 1/n of 180 degrees, where n is the number of light sources or the number of light source groups having different times at which the light emission output reaches a peak.

21. The light irradiation apparatus according to claim 13, wherein the arrangement of said light sources having different times at which the light emission output reaches a peak includes an arrangement of m-gon, where m is an integer multiple of n and n is the number of light sources or the number of light source groups having different times at which the light emission output reaches a peak.

22. The light irradiation apparatus according to claim 13, wherein the arrangement of said light sources having different times at which the light emission output reaches a peak is linear.

23. The light irradiation apparatus according to claim 13, wherein the arrangement of said light sources having different times at which the light emission output reaches a peak is set in such a way that when the number of light sources or the number of light source groups having different times at which light emission output reaches a peak is 2, the ratio of a sum total of irradiation light quantities of light sources or light source groups having different times at which one light emission output reaches a peak to a sum total of irradiation light quantities of light sources or light source groups having different times at which other light emission outputs reach a peak is 0.82 to 1.22 as a standard for an object to be irradiated.

24. The light irradiation apparatus according to claim 13, wherein the arrangement of said light sources having different times at which the light emission output reaches a peak is set in such a way that when the number of light sources or the number of light source groups having different times at which light emission output reaches a peak is 3, the ratio of a sum total of irradiation light quantities of light sources or light source groups having different times at which one light emission output reaches a peak to a sum total of irradiation light quantities of light sources or light source groups having different times at which other light emission outputs reach a peak is 1:0.75 to 1.33 as a standard for an object to be irradiated.

25. The light irradiation apparatus according to claim 13, wherein said semiconductor device is a solar cell.

26. A method of testing characteristics of a semiconductor device with a light irradiating step, comprising a step of irradiating the semiconductor device with light resulting from superimposed light rays from a plurality of light sources including light sources with different times at which light emission output reaches a peak.

27. The characteristic testing method according to claim 26, wherein said light sources having different times at which the light emission output reaches a peak are light sources including a plurality of light-emitting seeds with different time constants.

28. The characteristic testing method according to claim 26, wherein said light sources having different times at which the light emission output reaches a peak are discharge lamps.

29. The characteristic testing method according to claim 28, wherein said discharge lamps are mercury lamps or metal halide lamps.

30. The characteristic testing method according to claim 26, wherein the output waveforms of said light sources having different times at which the light emission output reaches a peak are substantially similar.

31. The characteristic testing method according to claim 26, wherein the output waveforms of said light sources having different times at which the light emission output reaches a peak are substantially periodic.

32. The characteristic testing method according to claim 26, wherein energy supply sources of said light sources having different times at which the light emission output reaches a peak are single-phase AC, two-phase AC or three-phase AC.

33. The characteristic testing method according to claim 26, wherein the phase difference of light emission output peaks of said light sources having different times at which the light emission output reaches a peak is an integer multiple of 1/n of 180 degrees, where n is the number of light sources or the number of light source groups having different times at which light emission output reaches a peak.

34. The characteristic testing method according to claim 26, wherein the arrangement of said light sources having different times at which the light emission output reaches a peak includes an arrangement of m-gon, where m is an integer multiple of n and n is the number of light sources or the number of light source groups having different times at which the light emission output reaches a peak.

35. The characteristic testing method according to claim 26, wherein the arrangement of said light sources having different times at which the light emission output reaches a peak is linear.

36. The characteristic testing method according to claim 26, wherein the arrangement of said light sources having different times at which the light emission output reaches a peak is set in such a way that when the number of light sources or the number of light source groups having different times at which light emission output reaches a peak is 2, the ratio of a sum total of irradiation light quantities of light sources or light source groups having different times at which one light emission output reaches a peak to a sum total of irradiation light quantities of light sources or light source groups having different times at which other light emission outputs reach a peak is 0.82 to 1.22 as a standard for an object to be irradiated.

37. The characteristic testing method according to claim 26, wherein the arrangement of said light sources having different times at which the light emission output reaches a peak is set in such a way that when the number of light sources or the number of light source groups having different times at which light emission output reaches a peak is 3, the ratio of a sum total of irradiation light quantities of light sources or light source groups having different times at which one light emission output reaches a peak to a sum total of irradiation light quantities of light sources or light source groups having different times at which other light emission outputs reach a peak is 1:0.75 to 1.33 as a standard for an object to be irradiated.

38. The characteristic testing method according to claim 26, wherein said semiconductor device is a solar cell.

* * * * *

UNITED STATES PATENT AND TRADEMARK OFFICE

CERTIFICATE OF CORRECTION

PATENT NO. : 7,425,457 B2 
APPLICATION NO. : 10/792715
DATED : September 16, 2008
INVENTOR(S) : Nobuo Tokutake et al.

It is certified that error appears in the above-identified patent and that said Letters Patent is hereby corrected as shown below:

COLUMN 1:
Line 39, "methods" should read -- the methods --.

COLUMN 4:
Line 54, "source," should read -- sources, --;
Line 54, "system" should read -- systems --; and
Line 55, "system." should read -- systems. --.

COLUMN 6:
Line 23, "superimpose" should read -- superimposed --.

COLUMN 7:
Line 5, "superimpose" should read -- superimposed --;
Line 17, "arrangement" should read -- arrangements --;
Line 20, "obtain" should read -- obtains --;
Line 31, "combine" should read -- combines --; and
Line 33, "combine" should read -- combines --.

COLUMN 9:
Line 28, "without-specially" should read -- without specially --.

COLUMN 10:
Line 53, "object." should read -- objects. --.

COLUMN 15:
Line 16, "plurality" should read -- plurality of --.

UNITED STATES PATENT AND TRADEMARK OFFICE
CERTIFICATE OF CORRECTION

PATENT NO. : 7,425,457 B2
APPLICATION NO. : 10/792715
DATED : September 16, 2008
INVENTOR(S) : Nobuo Tokutake et al.

It is certified that error appears in the above-identified patent and that said Letters Patent is hereby corrected as shown below:

COLUMN 16:
Line 26, "plurality" should read -- plurality of --.

Signed and Sealed this

Tenth Day of March, 2009

JOHN DOLL
*Acting Director of the United States Patent and Trademark Office*